United States Patent [19]

Itoh et al.

[11] 4,235,883

[45] Nov. 25, 1980

[54] NOVEL ANTIBIOTIC BN-213 SUBSTANCE AND ITS PRODUCTION

[75] Inventors: Jiro Itoh; Shinji Miyadoh, both of Yokohama; Mitsugu Itoh, Machida; Norio Ezaki, Yokohama; Tomizo Niwa, Yokohama; Yujiro Yamada, Yokohama, all of Japan

[73] Assignee: Meiji Seika Kaisha Limited, Tokyo, Japan

[21] Appl. No.: 950,822

[22] Filed: Oct. 12, 1978

[30] Foreign Application Priority Data

Oct. 31, 1977 [JP] Japan ................................. 52-129700

[51] Int. Cl.² ............................................. A61K 35/00
[52] U.S. Cl. ..................................... 424/122; 435/170

[58] Field of Search ...................... 424/122; 195/80 R; 435/170

[56] References Cited

U.S. PATENT DOCUMENTS 3,780,172  12/1973  Takeda et al. ....................... 424/122
4,038,384  7/1977   Berg et al. ............................ 424/122

*Primary Examiner*—Jerome D. Goldberg
*Attorney, Agent, or Firm*—Oblon, Fisher, Spivak, McClelland & Maier

[57] ABSTRACT

A BN-213 substance-producing strain of the genus Pseudomonas is cultivated to produce BN-213 substance in a culture medium. The BN-213 substance is isolated from the culture medium and purified, and proved to be a novel antibiotic.

4 Claims, 2 Drawing Figures

NOVEL ANTIBIOTIC BN-213 SUBSTANCE AND ITS PRODUCTION

BACKGROUND OF THE INVENTION

1. Field of the Invention

The present invention relates to a novel antibiotic substance and to a process for preparing same. More particularly, it relates to a novel antibiotic BN-213 substance produced by cultivating a BN-213 substance-producing strain of the genus Pseudomonas in a culture medium and recovering the BN-213 substance from the culture medium, and to a process for preparing same.

2. Prior Art

Known antibiotic substances whose chemical properties are similar to those of the BN-213 substance include Albocycline (The Journal of Antibiotics, Vol. 20, pp. 261-266, 1967), Conocandin (Helvetica Chemica Acta, Vol. 59, pp. 2506-2514, 1967), Chilaphylin (The Journal of Antibiotics, Vol. 26, pp. 126-130, 1973), and a new antibiotic substance 5057 (Japanese Patent Appln., Laid-Open No. 108902/1977). However, these are different from the BN-213 substance of the present invention as evidenced hereinafter.

BRIEF SUMMARY OF THE INVENTION

The novel antibiotic BN-213 substance of the present invention is produced by cultivating a BN-213 substance-producing strain of the genus Pseudomonas. According to the present invention, the producing strains are cultivated in a medium commonly used for cultivation or fermentation of microorganism, at 20° to 35° C.

The BN-213 substance of the present invention is effective in inhibiting growth of Gram-positive bacteria but shows low toxicity against animals, and is useful as antibacterial pharmaceuticals or raw materials thereof.

DETAILED DESCRIPTION OF THE INVENTION

Figure 1:
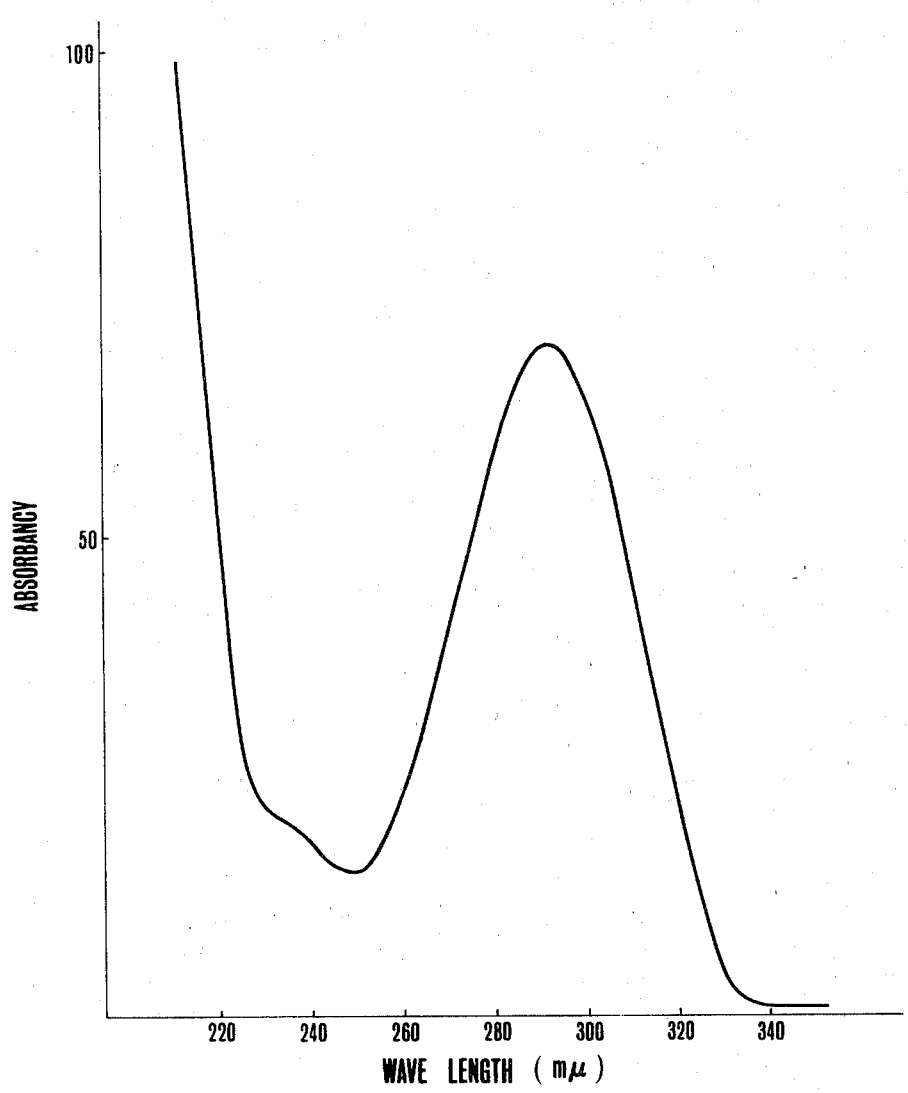
FIG. 1 is the ultraviolet absorption spectrum of the BN-213 substance of the present invention obtained in a test in which the substance was dissolved in methanol to a concentration of 25 mcg/ml before measurement.

The present inventors recognized that when a strain belonging to the genus Pseudomonas was cultivated, a substance which exhibits an antibacterial action against Gram-positive bacteria was present in the medium and that, after isolation, purification and characterization, this substance was a novel antibiotic different from any one which had been known. This substance was named BN-213 substance. The present invention is thus accomplished.

An example of the strains of the genus Pseudomonas used in the present invention is the strain of the genus Pseudomonas BN-213 newly isolated from a soil sample collected in Gunma-ken, Japan. This strain is deposited in the American Type Culture Collection (ATCC) under the number 31421, as well as in the Fermentation Research Institute, Agency of Industrial Science and Technology, Ministry of International Trade and Industry of Japan under the number FERM-P 4227.

The bacteriological characteristics of the genus Pseudomonas BN-213 strain are as follows (a) Morphological characteristics:

Cells grown in bouillon agar are 0.6–0.8×2.0–3.0μ bacilli which move using cirrus-like flagella. They form no spore, exhibiting no polymorphism and being Gram-negative.

(b) Cultural characteristics:

(1) Bouillon agar culture: Cells become brown and grow showing a creamlike appearance. Colonies show no noticeable wrinkle-like growth, viscosity and wandering tendency, and produce no diffusive pigment.

(2) Bouillon culture: The medium becomes turbid throughout. A bacterial film is formed on the liquid surface.

(3) Bouillon gelatin stab culture: Laminar liquefication (4) Milk culture: Liquefication with alkalization Physiological characteristics:

(1) Reduction of nitrate: Negative
(2) Denitrification: Negative
(3) Methyl red test: Negative
(4) VP(Voges-Proskauer) test: Negative
(5) Production of indole: Negative
(6) Production of hydrogen sulphide: Negative
(7) Hydrolysis of starch: Negative
(8) Utilization of citric acid (Simmonds' method): Positive
(9) Growth occurs with ammonium salts as the exclusive nitrogen source.
(10) Production of pigments: Yellow-green, water-soluble and fluorescent pigments are produced.
(11) Oxidase test: Positive
(12) Vitellus reaction: Positive
(13) Arginine decomposition: Positive
(14) Formation of levan: Positive
(15) Accumulation of poly-β-hydroxy butyric acid: Negative
(16) No demand for nutrients
(17) Growth temperature: 10° C.-30° C.; No growth at 41° C.
(18) No growth under an anaerobic condition
(19) O-F test (Heuleifson's method): O type
(20) Utilization of carbon sources:
  (i) Growth occurs with the following compounds of carbon as the exclusive carbon sources: Glucose, trehalose, 2-ketogluconic acid, L-valine, β-alanine, DL-arginine, L-arabinose, xylose, saccharate
  (ii) The following compounds of carbon cannot be utilized as the exclusive carbon sources: Maltose, starch, lactose, adonite, geraniol, Sorbitol, sucrose Comparing the above-mentioned bacteriological characteristics of the BN-213 strain with the identified strains listed in Bergey's Manual of Determinative Bacteriology, 8th Edition, 1974, the following conclusion was obtained:

1. This strain belongs to the genus Pseudomonas, since it is of Gram-negative bacilli incapable of producing spores, with cirrus-like flagella and absolutely aerobic;
2. In consideration of no demand for nutrients, no accumulation of poly-β-hydroxybutyric acid in bacterial bodies, production of fluorescent pigments and the carbon source utilization pattern, the BN-213 strain well coincide with genus *Pseudomonas fluorescence* (the genus Pseudomonas 3-5 listed in the above literature, page 220, Table 7-1).

3. Compared with the contents of Table 7-2 in the above literature, page 221, the BN-213 strain is slightly different from each biotype of the genus *Pseudomonas fluorescence*, and no biotype is found which perfectly coincide with the BN-213 strain.

Accordingly, the present inventors named this strain Pseudomonas sp. BN-213.

According to the present invention, the process for preparing the novel antibiotic BN-213 substance may use various culture media usually used for the fermentation of common microoganisms. Examples of the carbon source include glucose, dextrin, millet jelly, etc. Examples of the nitrogen source include peptone, meat extract, powdered bouillon, soybeam powder, corn steep liquor, ammonium sulphate, ammonium chloride, etc. If required, inorganic salts, such as sodium chloride and calcium carbonate, and antifoaming agents may be added to the medium.

For cultivation, the methods which use liquid media are suitable, such as shake culture and submerged aerationagitation culture. Proper cultivation temperature is 20°–35° C., and proper cultivation period is 1–3 days.

Methods for the assay of BN-213 substance in the present invention are as follows The assay medium contained a mixture of 2% MYCINAGAR (produced by Kyoei Seiyaku Co., Ltd.) and 0.5% BACTOAGAR (produced by DIFCO Co., Ltd.) A strain of *Bacillus subtilis* ATCC 6633 was used as test organism.

The results of the assay of BN-213 substance (pure) showed that within the concentration range of 500 mcg/ml to 2,000 mcg/ml thereof, a linear relationship existed between the logarithm of said concentration and the diameter of inhibition zones; said inhibition zone diameters ranged from 9.0 to 11.0 mm (paper disc method).

BN-213 substance has the physical and chemical properties to be given later, and therefore can be extracted and purified according to these properties. For this purpose, the following process is effective.

First, solid parts are removed from the cultured substance containing active constituents by filtration. Then the active substance are extracted from the filtrate with ethyl acetate, being concentrated to obtain an oily crude BN-213 substance. This crude BN-213 substance is further purified using a proper combination of silica gel, alumina, gel-filtration material, and the like to obtain a purified BN-213 substance.

The purified BN-213 substance thus obtained was subjected to thin-layer chromatography using various solvent systems. With each solvent system, a single spot appeared. Therefore, it is recognized that the abovementioned purified BN-213 substance is perfectly pure.

Figure 2:
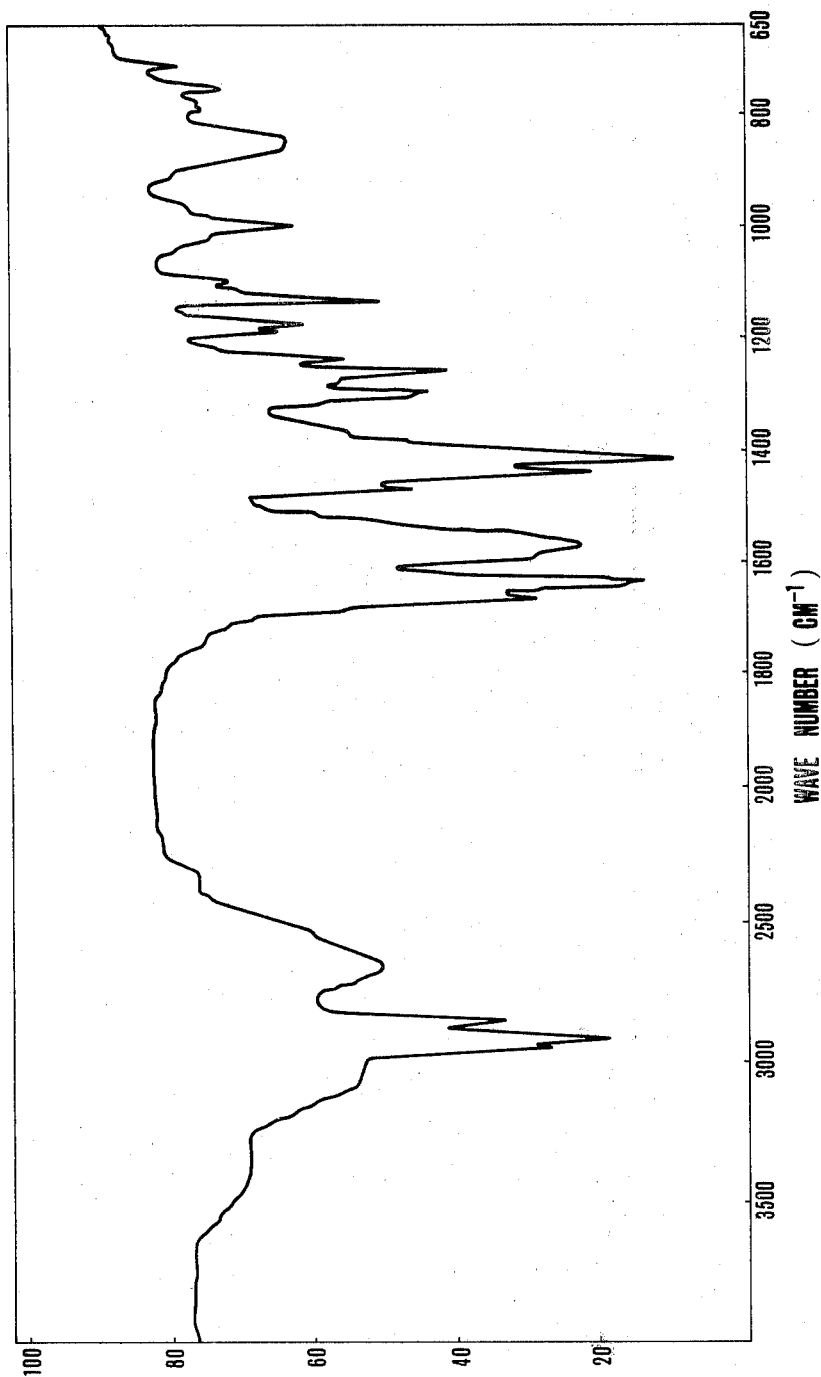
FIG. 2 is the infrared absorption spectrum of the BN-213 substance of the present invention measured by the use of tablets produced by mixing the substance with potassium bromide.

The physical and chemical properties of the BN-213 substance are as follows:

1. Elementary analysis: C: 73.93%, H: 10.28%, O: 15.79% (Difference)
2. Molecular weight: 294 (High resolution mass spectroscopy)
3. Molecular formula: $C_{18}H_{30}O_3$
4. Melting point: 84° C.
5. Specific rotatory power: $[\alpha]_D^{20}$ 0° (C=0.4, methanol)
6. Ultraviolet absorption spectrum: The spectrum measured in methanol is shown in FIG. 1: Characteristic absorption maximum at 292 m$\mu$
7. Infrared absorption spectrum: The spectrum measured by the potassium bromide tablet method is shown in FIG. 2: Characteristic absorption bands at 2920, 2850, 2650, 1660, 1630, 1570, 1440, 1405, 1300, 1260, 1240, 1170, 1130, 1000, 850, 760, 720 (cm$^{-1}$)
8. Solubility: Soluble in methanol, ethyl acetate and aceton, and insoluble in water and chloroform. 9. Color reaction:

Ninhydrin reaction: Negative
Sakaguchi's reaction: Negative
Ferric chloride reaction: Negative
Sulfuric acid reaction: Positive
Potassium permanganate reaction: Positive 10. Rf values in silica gel thin-layer chromatography

| Solvent system | Rf value |
| --- | --- |
| Chloroform:Methanol (5:1) | 0.81 |
| Benzene:Ethyl acetate (5:1) | 0.52 |
| Benzene:Aceton (20:1) | 0.23 |
| n-Butanol:Methanol:Water (4:1:2) | 0.79 |

The activities of the BN-213 substance against various microorganisms are given in Tagle 1. From Table 1, it is understood that the BN-213 substance is useful as antibacterial pharmaceuticals or raw materials thereof. In an acute toxicity test, a dose of 50 mg/kg of the BN-213 substance administered intravenously to mice resulted in survival of all the test mice.

A dose of 10–100 mg/kg of the BN-213 substance may be administered to human body by intramuscular injection, hypodermic injection or venous injection. It also may be applied to a medicine for external use.

TABLE 1

| Test organism | MIC (mcg/ml) |
| --- | --- |
| Staphylococcus aureus 209-P JC-1 | 12.5 |
| Staphylococcus aureus Smith S-424 | 12.5 |
| Staphylococcus aureus No.26 | 12.5 |
| Staphylococcus aureus N-0041 | 12.5 |
| Staphylococcus epidermidis N-0015 | 25 |
| Bacillus subtilic ATCC 6633 | 12.5 |
| Bacillus anthracis No.119 | 3.13 |
| Escherichia coli NIHJ JC-2 | >100 |
| Proteus vulgaris OX 19 | >100 |

Known antibiotic substances whose chemical properties are similar to those of the BN-213 substance include Albocycline (The Journal of Antibiotics, vol. 20, pp. 261–266, 1967), Conocandin (Helvetica Chemica Acta, vol. 59, pp. 2506–2514, 1967), Chilaphylin (The Journal of Antibiotics vol. 26, pp. 126–130, 1973), and a new antibiotic substance 5057 (Japanese Patent Appln., Laid-Open No. 108902/1977).

For example, the melting point of BN-213 substance is 84° C., which is nearly equal to that of Albocycline (83°–84° C.). However, Albocycline exhibit no ultraviolet absorption spectrum, and its specific rotatory power is $[\alpha]_D^{20}-90°$ (C=1, methanol); therefore Albocycline is different from the BN-213 substance in these points. Conocandin has the same molecular formular as the BN-213 substance, but exhibits no ultraviolet absorption spectrum and its specific rotatory power is $[\alpha]_D^{20}-7\pm1°$ (C=0.557, methanol); therefore, Conocandin is different from the BN-213 substance. Though Chilaphylin has an elementary composition similar to that of the BN-213 substance, its characteristic ultraviolet-absorption maximum is at 225 mμ and its specific rotatory power is $[\alpha]_D^{20} + 38°$ (C=0.1, chloroform); therefore it is different from the BN-213 substance. In the case of the new antibiotic 5057, its characteristic ultraviolet-absorption maximum is at 292 mμ as with the BN-213 substance, but its melting point is 133° to 135° C. and its molecular weight is 664 to 666; therefore, it also differs from the BN-213 substance. Accordingly, the BN-213 substance is recognized as a new and novel antibiotic substance. Among the compounds chemically synthesized, there is also none which perfectly corresponds to the BN-213 substance.

The present invention will be understood more readily by reference to the following examples; however, these examples are intended to illustrate the invention and not to be construed to limit the scope of the invention.

EXAMPLE 1

A liquid medium containing 2% wheat germ, 3% glycerin, 0.4% ammonium acetate and 0.4% calcium carbonate were poured into twenty 500 ml Sakaguchi flasks separately, 100 ml for each. Then the flasks were sealed with cotten, being sterilized at 120° C. for 10 minutes under pressure before inoculated from a slant culture of the BN-213 strain, each by the amount capable of being carried by a platinum loop at a time. The culture thus inoculated on the medium was cultivated with shaking at 28° C. for two days. As a result, 1.8 liters of a liquid medium containing 80 μg/ml of BN-213 substance was obtained.

Solid parts were then removed from this liquid medium by filtration. The filtrate was adjusted to pH 2.0 with hydrochloric acid. Then the active substance was extracted with 1.8 liters of ethyl acetate. This ethyl acetate was concentrated under a reduced pressure until 380 mg of BN-213 substance in the form of brown oily stuff was obtained.

This oily stuff was placed on a 80 ml column of WAKOGEL C-200 (produced by Wako Seiyaku Co., Ltd.) previously filled with chloroform, being developed with chloroformmethanol system solvents stepwise increased in methanol content. The active fractions were concentrated under a reduced pressure to obtain 34.5 mg of powder. This powder was dissolved in methanol, being adsorbed on a small amount of WAKOGEL C-200. Then, it was placed on a 20 ml column of WAKOGEL C-200 previously filled with benzene, being developed with benzene-ethylene acetate system solvents stepwise increased in ethyl acetate content. The active fractions were concentrated to obtain 11.5 mg of white powder.

EXAMPLE 2

20 liters of a culture medium containing 2% wheat germ, 3% glycerin, 0.4% ammonium chloride and 0.4% calcium carbonate were introduced in a 30 liter culture tank, being sterilized at 120° C. for 15 minutes. After cooled, the culture tank was innoculated with a seed culture of the BN-213 strain that had been previously cultivated on the same medium in a Sakaguchi flask for two days. The medium in the tank was cultivated under aeration and stirring (Aeration rate: 15 liters/min., Stirring speed: 200 rpm) at 28° C. for two days to obtain 17 liters of a liquid medium containing 100 μg/ml of BN-213 substance.

Solid parts were removed from this liquid medium by filtration, and the filtrate was adjusted to pH 2.0 with hydrochloric acid. Then the active substance was extracted with 20 liters of ethyl acetate. Afterwards, the ethyl acetate was concentrated under an reduced pressure until 3.97 g of BN-213 substance in the form of brown oily stuff was obtained.

This oily stuff was placed on a 270 ml column of WAKOGEL C-200 (produced by Wako Seiyaku Co., Ltd.) previously filled with chloroform, being developed with chloroform-methanol system solvents stepwise increased in methanol content. The active fractions were concentrated under a reduced pressure to obtain 630 mg of powder.

This powder was dissolved in methanol, being adsorbed on a small amount of WAKOGEL C-200. Then, it was placed on a 200 ml column of WAKOGEL C-200 previously filled with benzene, being developed with benzene-ethylene acetate system solvents stepwise increased in ethyl acetate content. The active fractions were concentrated to obtain 101.5 mg of white powder.

What is claimed is:

1. An antibiotic BN-213 substance, which is effective in inhibiting the growth of Gram-positive bacteria and having the following properties:
   Elementary analysis: C. 73.93%; H. 10.28%; O. 15.79% (Difference);
   Molecular weight: 294 (High resolution mass spectrometry)
   Molecular formula: $C_{18}H_{30}O_3$;
   Specific rotatory power: $[\alpha]_D^{20}$ 0° (C=0.4, methanol);
   Melting point: 84° C.;
   Ultraviolet absorption spectrum: Characteristic absorption maximum at 292 mμ in $CH_3OH$;
   Infrared absorption spectrum: Characteristic absorption bands at 2920, 2850, 2650, 1660, 1630, 1570, 1440, 1405, 1300, 1260, 1240, 1170, 1130, 1000, 850, 760, 720 ($cm^{-1}$).

2. A process for preparing an antibiotic substance from Pseudomonas sp. BN-213, ATCC No. 31421 as defined in claim 1 which comprises the steps of;
   cultivating said BN-213 Pseudomonas strain in a culture medium containing sources of assimilable carbon and assimilable nitrogen, and if required, inorganic salts and antifoaming agent, which support growth of said strain and enhence production of said antibiotic, at approximately pH 2 at 20° C. to 35° C. until a sufficient amount of antibiotic is formed, and
   recovering said antibiotic from the culture medium.

3. A process according to claim 2, wherein the source of assimilable carbon is glucose, dextrin or millet jelly, and the source of assimilable nitrogen is peptone, meat extract, powdered bouillon, soybean powder, corn steap liquor, ammonium sulphate or ammonium chloride, and the inorganic salts are selected from the group consisting of sodium chloride and calcium carbonate.

4. A process according to claim 2, wherein said antibiotic is extracted from the filtrate with ethyl acetate and subjected to purification by the use of a proper combination of silica gel, alumina and gel-filtration material to obtain a purified BN-213 substance.

* * * * *